United States Patent [19]

Kannan et al.

[11] Patent Number: 5,126,233
[45] Date of Patent: Jun. 30, 1992

[54] OIL SOLUBLE COLOR PRECURSOR INVOLVING CERTAIN CRYSTALLINE 6-PHENYL PYRIDINE DERIVATIVES

[75] Inventors: Ramamurthi Kannan, Cincinnati; Steven L. Yeager, Miamisburg, both of Ohio

[73] Assignee: The Mead Corporation, Dayton, Ohio

[21] Appl. No.: 658,066

[22] Filed: Feb. 20, 1991

[51] Int. Cl.⁵ .................. B41M 5/20; C07D 213/24; G03C 1/73
[52] U.S. Cl. ................................ 430/340; 430/211; 430/235; 430/343; 430/962; 503/218; 546/334
[58] Field of Search .............. 546/334; 503/218; 430/340, 211, 235, 343, 962

[56] References Cited

U.S. PATENT DOCUMENTS

| | | |
|---|---|---|
| 3,985,376 | 10/1976 | Baumann et al. .................. 427/150 |
| 4,399,209 | 8/1983 | Sanders et al. .................. 430/138 |
| 4,440,836 | 4/1984 | Bailey .................. 429/48 |
| 4,576,891 | 3/1986 | Adair et al. .................. 430/138 |
| 4,600,678 | 7/1986 | Adair et al. .................. 430/138 |
| 4,772,541 | 9/1988 | Gottschalk et al. .................. 430/339 |
| 4,842,976 | 6/1989 | Sander et al. .................. 430/138 |
| 4,908,447 | 3/1990 | Mayer et al. .................. 546/194 |
| 4,962,010 | 10/1990 | Colyer et al. .................. 430/138 |

OTHER PUBLICATIONS

Chemical Abstracts, vol. 109, No. 9, Abstract 75,206z, p. 96, Aug. 29, 1988.

*Primary Examiner*—Alan L. Rotman
*Assistant Examiner*—Celia Chang
*Attorney, Agent, or Firm*—Thompson, Hine and Flory

[57] ABSTRACT

This invention is directed to a compound which is 4-(4'-(N',N'-dimethylamino)phenyl)-2-(2'-n-octyloxyphenyl)-6-phenyl pyridine.

6 Claims, No Drawings

OIL SOLUBLE COLOR PRECURSOR INVOLVING CERTAIN CRYSTALLINE 6-PHENYL PYRIDINE DERIVATIVES

BACKGROUND OF THE INVENTION

The present invention generally relates to a novel pyridine compound. More particularly, but not by way of limitation, the present invention discloses the pyridine compound employed as a yellow color former.

Recording materials which employ microencapsulated leuco dyes as color formers are now well known in the art. They include carbonless paper, thermal recording papers and recently cylithographic recording materials of the type described in U.S. Pat. No. 4,399,209. In each of these recording materials, it is desirable to use color formers which exhibit high oil solubility in order to obtain high image densities as the color formers are dissolved in oils to microencapsulate them.

Commonly assigned U.S. Pat. No(s). 4,440,836, 4,842,976, 4,600,678 and 4,576,891 describe cylithographic materials which comprise a polyester film base with a layer of light sensitive microcapsules which are sensitive to red, green and blue light, and are incorporated by reference herein. Image-wise exposure of the material to actinic radiation allows for a colored image to be formed.

U.S. Pat. No. 4,908,447 discloses unsymmetrical 2-,6-diphenyl-4-(4-aminophenyl)pyridine compounds useful as dye precursors. Particularly disclosed is 2-(2-methoxyphenyl)-4-(4-dimethylaminophenyl)-6-phenyl pyridine.

U.S. Pat. No. 3,985,376 discloses yellow dye precursors for pressure-sensitive recording material. This patent teaches of symmetrical 4-(4'-aminophenyl)-pyridines. In one embodiment, 4-(4'-dimethylaminophenyl)-2,6-diphenylpyridine is disclosed. U.S. Pat. No. 4,600,678 discloses the use of this precursor in the aforementioned cylithographic materials. In another embodiment, 4-(4'-aminophenyl)-2,6-(4',4'-dimethoxyphenyl)-pyridine is disclosed. While the dye precursors described in the aforementioned patents are useful in pressure-sensitive recording systems, there is a need for improvement in their solubility, color, and the ease with which they can be manufactured. There is also a need for dye precursor which aids in obtaining faster film speed and dynamic range in the imaging field. It is therefore desirable that there be a dye precursor which while still retaining good solubility and color, provides increased manufacturing ease.

SUMMARY OF THE INVENTION

The present invention relates to the color former 4-(4'-N',N'-dimethylaminophenyl)-2-(2-octyloxyphenyl)-6-phenyl pyridine.

Experience had demonstrated that when long carbon chains are introduced into a triphenylpyridine, the compound is isolated as an oil and the use of solvents and tedious procedures are required to recover and purify the compound as a solid. Surprisingly, the present invention provides a compound which readily crystallizes and thus simplifies the manufacturing process. At the same time, the compound possesses excellent solubility in the oils employed in carbonless paper and the monomers used in cylithographic materials.

For example, this compound dissolves very quickly in TMPTA at 60° C. to provide a 15% by weight solution in TMPTA. In contrast, powdered 4-(4'-dimethyl aminophenyl)-2,6-diphenyl pyridine dissolves with difficulty to the extent of 10% at 60° C. and the 2'-ethoxy only to 2%. Such excellent solubility of title compound in the monomer at low temperature allows us to prepare the internal phase without risking premature polymerization due to excessive heating to higher temperatures during the process of dissolving the color precursor.

Further objects of the present invention are to employ the compound with other dyes in a carbonless or cylithographic system to give a good black and in a color system to give true colors. Cylithographic systems are described in U.S. Pat. No. 4,399,209. The compound is used in an amount which provides the desired density or color hue and can be readily determined.

It is another object of this invention to provide a yellow color former compound which aids in manufacturing processability, exhibits good solubility and color. Numerous other objects, features and advantages of the present invention will be readily apparent to those skilled in the art upon reading the following disclosure.

DETAILED DESCRIPTION

Preparation of 2-(2'-n-octyloxy)phenyl-(4'-N',N'-dimethylamino)phenyl-6-phenyl pyridine.

Phenacylpyridinium chloride was prepared by reacting 424 grams chloroacetophenone with 322 ml pyridine by dropwise adding the pyridine to the former in 1400 ml acetonitrile at 65° C. A crystalline mass was obtained which was heated to 70° C. and allowed to cool to 10° C., then filtered and washed with 500 ml acetonitrile. The dried product (626.5g) had a melting point of 203-206° C.

A mixture of approximately 264 grams of 4-dimethylamino-benzaldehyde, approximately 440 grams of 2-n-octyloxy-acetophenone (prepared from approximately 258.7 gms 2'-hydroxy acetophenone and approximately 381.6 gms of bromooctane), approximately 414 gms of phenacylpyridinium chloride, approximately 590 grams of ammonium acetate and approximately 885 ml of glacial acetic acid were mixed in a 3 liter 3-neck flask heated to approximately 125 to 135° C. and held for approximately 5 hours. The mixture was then cooled to approximately 25° C. and the solids were separated by filtration. The solids were washed with 500 ml portions of methanol three times each. The solids were then dissolved in 1500 ml toluene, and the toluene phase was washed 3 times each with 500 ml of water. The toluene extract was dried by azeotropic distillation and treated with activated carbon (15 gms) and filtered. The filtrate was concentrated and the residue taken up in 1500 ml methanol. The separated product was filtered, washed with methanol repeatedly to a light yellow color and dried at 25° C. The weight of the recovered compound was 540.8 gms, 63.8% of theory and had a m.p. 91-92°.

The present invention is shown by the following non-limiting example and comparative example, which show the internal phase composition as used in cylithographic systems such as the one in Gottschalk U.S. Pat. No. 4,772,541. As can be seen from the example, the 2-2'-n-octyloxy)phenyl(4'-N',N'-dimethylamino)phenyl-6-phenyl pyridine provides greater dynamic range and decreased gamma. This provides for better tone in the product.

EXAMPLE

The internal phase is made up of 130 g TMPTA (trimethylolpropane triacrylate), 20 g DPHPA dipentaerythritol hydroxypentaacrylate), 0.9 g 7-diethylamino-3-cinnamoylcoumarin, 1.5 g DIDMA (diisopropyldimethylaniline), 18 g 2-(2'-n-octyloxy)phenyl-(4'-N',N'-dimethylamino)phenyl-6-phenyl pyridine, 10 g isocyanate, and 1.5 g THEEDA (N,N,N',N'tetrakis(2-hydroxyethyl)ethylene diamine. This internal phase was emulsified, encapsulated and coated on a polyester film base essentially as described in U.S. Pat. No. 4,962,010, issued Oct. 9, 1990. Upon exposing the coated substrate to actinic radiation, the following photofunctionalities were obtained: Dmax 2.15, Dmin 0.11, Log E D10 3.60, Log E D90 3.12, Dynamic Range 0.48 and Gamma 3.39.

COMPARATIVE EXAMPLE

The internal phase here is made in the identical fashion as Example 1, with the exception that 18 g of 4-(4'-dimethylaminophenyl)-2,6-diphenylpyridine was used in place of the 18 g 2-(2'-n-octyloxy)phenyl-(4'-N',N-dimethylamino)phenyl-6-phenyl pyridine. Upon exposure, it gave the following photofunctionalities: Dmax 2.17, Dmin 0.11, Log E D10 3.62, Log ED90 3.18, Dynamic Range 0.44 and Gamma 3.83.

Having described the invention in detail and by reference to preferred embodiments thereof, it will be apparent that the modifications and variations are possible without departing from the scope of the invention defined in the appended claims.

What is claimed is:

1. The compound which is 4-(4'-(N',N'-dimethylamino)phenyl)-2-(2'-n-octyloxyphenyl)-6-phenyl pyridine.

2. A composition containing color precursors which provide a black image when developed wherein said composition includes 4-(4'-(N',N'-dimethylamino)phenyl)-2-(2'-n-octyloxyphenyl)-6-phenylpyridine.

3. The composition of claim 2 wherein said composition is useful in a carbonless duplicating system.

4. The composition of claim 2 wherein said composition is useful in a cylithographic system.

5. The compound of claim 1 wherein said compound is crystalline.

6. The composition of claim 2 wherein said 4-(4'-N',N'-dimethylamino)phenyl)-2-(2'-n-octyloxyphenyl)-6-phenylpyridine is crystalline.

* * * * *